US012419717B2

(12) United States Patent
Weisser et al.

(10) Patent No.: US 12,419,717 B2
(45) Date of Patent: Sep. 23, 2025

(54) FASTENING CLAMP FOR ATTACHING HOLDERS FOR MEDICAL INSTRUMENTS IN A STERILIZATION MESH BASKET, AND ARRANGEMENT HAVING A STERILIZATION MESH BASKET AND A FASTENING CLAMP

(71) Applicant: Aesculap AG, Tuttlingen (DE)

(72) Inventors: Daniel Weisser, Villingen-Schwenningen (DE); Eva Streit, Bodman-Ludwigshafen (DE); Timo Knittel, Wurmlingen (DE); Hermann Deutscher, Neuhausen ob Eck (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/880,902

(22) PCT Filed: Aug. 31, 2023

(86) PCT No.: PCT/EP2023/073892
§ 371 (c)(1),
(2) Date: Jan. 3, 2025

(87) PCT Pub. No.: WO2024/047158
PCT Pub. Date: Mar. 7, 2024

(65) Prior Publication Data
US 2025/0186154 A1    Jun. 12, 2025

(30) Foreign Application Priority Data
Sep. 2, 2022  (DE) .................... 10 2022 122 236.5

(51) Int. Cl.
*A61B 50/33*    (2016.01)
*A61B 50/00*    (2016.01)
*A61B 50/20*    (2016.01)

(52) U.S. Cl.
CPC ........ *A61B 50/33* (2016.02); *A61B 2050/007* (2016.02); *A61B 50/20* (2016.02)

(58) Field of Classification Search
CPC .... A61B 50/33; A61B 2050/007; A61B 50/20
(Continued)

(56) References Cited

U.S. PATENT DOCUMENTS

| 11,596,492 | B2 * | 3/2023 | Baggaley | ............... A61B 50/20 |
| 2010/0176016 | A1 | 7/2010 | Pell | |

(Continued)

FOREIGN PATENT DOCUMENTS

| DE | 102005047187 A1 | 4/2007 |
| DE | 102017109869 A1 | 11/2018 |

(Continued)

OTHER PUBLICATIONS

Search Report received in International Application No. PCT/EP2023/073892 dated Nov. 30, 2023, with translation, 5 pages.

(Continued)

*Primary Examiner* — Todd M Epps
(74) *Attorney, Agent, or Firm* — Christopher A. Rothe; CM Law

(57) ABSTRACT

An arrangement includes a sterilization tray and a fixing clip configured for tool-free mounting on a perforated corrugated bottom of the sterilization tray. The fixing clip has a main section, on which two rows of arms are arranged opposite to one another with respect to a center axis. Each row of arms has a first holding arm and a second holding arm, on which a snap-in nose is respectively formed. The snap-in noses of the two holding arms of each row of arms point towards one another. A first edge extends on the main section between the first two holding arms and a second edge extends between the second two holding arms. A recess or notch is formed on each of the two edges, into which crosspieces can immerse.

10 Claims, 3 Drawing Sheets

(58) Field of Classification Search
USPC .............................. 248/689; 24/455; 206/363
See application file for complete search history.

(56) References Cited

U.S. PATENT DOCUMENTS

2020/0030049 A1* 1/2020 Oko ........................ A61L 2/26
2021/0338357 A1* 11/2021 Lenzenhuber ......... A61B 50/30

FOREIGN PATENT DOCUMENTS

DE 102018104938 A1 9/2019
EP 2860126 A1 4/2015

OTHER PUBLICATIONS

Search Report received in German Application No. 10 2022 122 236.5 dated Jul. 28, 2023, with translation, 7 pages.

* cited by examiner

FASTENING CLAMP FOR ATTACHING HOLDERS FOR MEDICAL INSTRUMENTS IN A STERILIZATION MESH BASKET, AND ARRANGEMENT HAVING A STERILIZATION MESH BASKET AND A FASTENING CLAMP

CROSS-REFERENCE TO RELATED APPLICATIONS

This application is the United States national stage entry of International Application No. PCT/EP2023/073892, filed on Aug. 31, 2023, and claims priority to German Application No. 2022 122 236.5, filed on Sep. 2, 2022. The contents of International Application No. PCT/EP2023/073892 and German Application No. 10 2022 122 236.5 are incorporated by reference herein in their entireties.

FIELD

The present disclosure relates to the attachment of storage elements or holders for medical instruments, in particular for minimally invasive surgery, in sterilization trays.

BACKGROUND

In minimally invasive surgery, medical instruments are provided and stored in sterilization trays. These sterilization trays with the instruments are placed in sealable sterilization containers and may also be stacked in them.

From the prior art, a sterilization tray of Applicant is known that is marketed under the registered trademark AICON®. When viewed in cross-section, it has a trapezoidal stepped corrugated base, which means that feet on the sterilization tray are no longer necessary. The corrugated base has a perforated grid, with the webs set at 45 degrees to the edge of the corrugated bottom and to the edge of the sterilization tray, respectively.

Moreover, it is known from the prior art to attach instrument holders to the upper side of the bottom of sterilization trays by means of fixing clips. These can also be shifted to increase flexibility. At https://endoskopie.bbraun.com/p/PRID00006221 on the internet, such a fixing clip of Applicant designated JG301R is disclosed. On a main section of the fixing clip, two rows of arms are arranged opposite each other with respect to a center axis, each row of arms having a first holding arm and a second holding arm on which a lateral snap-in nose is respectively formed, the snap-in noses of the two holding arms of each row of arms pointing towards one another. The holding arms of the fixing clips are inserted from below through the perforated grid of the bottom of the sterilization tray. The fixing clip is clipped onto the perforated grid by means of the snap-in noses. Subsequently, a silicone bar of the instrument holder can be pushed between the holding arms.

However, it has been shown that such fixing clips cannot be mounted horizontally on the corrugated bottom of a sterilization tray without feet (e.g. on the aforementioned tray marketed under the registered trademark AICON®) and that they protrude comparatively far downwards from the corrugated bottom, so that the sterilization tray, depending on the distribution of the fixing clips on the corrugated bottom, is not standing stable (e.g. in a sterilization container). Furthermore, the fastening clips that protrude downwards may scratch or even damage objects located underneath them (e.g. the bottom of the sterilization container).

SUMMARY

The object of the present disclosure is to provide a fixing clip for a corrugated bottom of a sterilization tray and an arrangement with a sterilization tray and at least one such fixing clip, in which the sterilization tray in question is standing stable in all configurations or positions of the fixing clips. Furthermore, the object located below (e.g. the bottom of the sterilization container) is not to be scratched or damaged by the fixing clip.

The fixing clip according to the disclosure is designed and laid out for tool-free fastening to a perforated corrugated bottom, preferably without feet, of a sterilization tray. The fixing clip has a main section on which two rows of arms are arranged opposite each other with respect to a center axis, each row of arms having a first holding arm and a second holding arm, on each of which a lateral snap-in nose is formed. The snap-in noses of the two holding arms of each row of arms point towards each other and serve to clip the fixing clip onto the perforated grid of the corrugated bottom. A first edge extends between the first two holding arms and a second edge extends between the second two holding arms on the main section of the fixing clip, transversely to the center axis. According to the invention, a recess or notch is formed on each of the two edges. This makes it possible for the main section of the mounted fixing clip not to protrude downwards out of the corrugated bottom, but to be completely immersed in the corrugated bottom from below, because lower crosspieces of the corrugated bottom are inserted from above into the recesses of the main section. This prevents the main section from scratching or damaging objects located below it (e.g. the bottom of a sterilization container).

Preferably, the two edges of the main section extend transversely to the center axis.

In a smaller version of the fixing clip, the two recesses or notches extend transversely to the center axis preferably over at least one third of a respective width of the main section or a respective distance of the holding arms (opposite to one another). This allows a crosspiece to immerse well into the respective recess and the fixing clip to be mounted particularly high and/or the main section to have an advantageous thickness, without the main section protruding downwards from the corrugated bottom.

In the smaller version of the fixing clip, the two recesses or notches each extend along the center axis preferably over at least one-eighth of the length of the main section. This allows a crosspiece to be immersed far into the respective recess and the fixing clip to be mounted particularly high and/or the main section to have the advantageous thickness without the main section protruding downwards from the corrugated bottom.

In a larger version of the fixing clip, an intermediate arm is provided, respectively, between the two holding arms of a row of arms. Furthermore, a further recess is provided approximately in the center of the main section, which is formed as a through recess. This allows a total of three crosspieces to be immersed into a respective recess. In the case of the larger version of the fixing clip, holding sections for a silicone bar preferably are also formed on the free end sections of the intermediate arms.

Preferably, holding sections for the silicone bar of an instrument holder are formed on free end sections of the holding arms and/or intermediate arms. Preferably, the holding sections are provided opposite to one another in pairs, preferably facing one another in pairs. In other words, preferably the holding sections of the first two holding arms point towards each other and/or the holding sections of the second two holding arms point towards each other and/or the holding sections of the intermediate arms point towards each other. In a simple design, both in terms of production and assembly, the fixing clip is a bent sheet metal part. In a further simple design, both in terms of production and assembly, the central axis is also an axis of symmetry.

In the first alternative of the larger version of the fixing clip, a further snap-in nose is provided on each of the two intermediate arms, which extends in the opposite direction of the snap-in nose of the first holding arm. Preferably, however, a further snap-in nose is also provided on each of the two intermediate arms, which extends in the opposite direction to the snap-in nose of the second holding arm. This allows two crosspieces to be held on both sides per row of arms, and holding of the fixing clip is improved.

In a second variant of the larger version, the intermediate arm is a lug without snap-in noses. In particular, for this purpose, a straight edge portion is formed on the opposite side of the snap-in noses of the two neighboring holding arms. Thus, per row of arms, two crosspieces likewise are clipped on, but only on one side of the snap-in nose of the holding arm. The two edge portions of each lug can be parallel to each other.

Mounting the fixing clip is simplified if a lead-in chamfer is formed above the snap-in noses on the four holding arms and, in the case of the first variant of the larger version of the fixing clip, also on the intermediate arms. Lead-in chamfers lying opposite each other can form funnel-shaped free spaces into which the crosspieces are inserted.

The arrangement according to the disclosure has a sterilization tray, which can be configured and laid out for insertion into a preferably feetless sterilization container. A corrugated bottom of the sterilization tray has a perforated grid, with four webs of the perforated grid forming crosspieces. The crosspieces are arranged at two different heights of the corrugated bottom. At least one of the afore-described fixing clips can be clipped or is clipped on to the corrugated bottom in a tool-free manner. The main section of the mounted fixing clip can immerse completely in the corrugated bottom from below because lower crosspieces of the corrugated bottom immerse into the recesses of the main section from above. Then, the main section does not protrude downwards out of the corrugated bottom, but immerses into it. This prevents the main section from scratching or damaging objects located underneath (e.g. the bottom of the sterilization container).

Preferably, the crosspieces are arranged in rows of crosspieces, which are arranged alternately on the two different heights, the rows of crosspieces extending along the entire corrugated bottom and parallel to one edge of the corrugated bottom or of the sterilization tray.

Between the two holding arms of each row of arms of the at least one fixing clip, one or two crosspieces of a row of crosspieces can be or are received. The one crosspiece or the two crosspieces rest against the snap-in noses and are held in this way. In the case of two crosspieces per row of arms, the intermediate arm of the larger version of the fixing clip extends between the two crosspieces.

In the smaller version of the fixing clip, two adjacent crosspieces of a lower row of crosspieces can each immerse into a recess or notch formed in the edge of the main section.

In the larger version of the fixing clip, three adjacent crosspieces of a lower row of crosspieces can each immerse into a recess in the main section. More specifically, two crosspieces immerse in the two recesses formed at the edge, while one crosspiece immerses in the middle recess formed as a through recess.

In a particularly preferred further development of the disclosed arrangement, the webs of the corrugated bottom are set at an angle of 45 degrees to the edge of the corrugated bottom or the sterilization tray. Due to the arrangement of the crosspieces between the holding arms of a row of arms, it is possible to fasten the (respective central axis of the) at least one fixing clip parallel or at 90 degrees to the edge of the corrugated bottom or the sterilization tray, despite the 45-degree angle of the webs on the upper side of the corrugated bottom. This also ensures that the silicone bar of the instrument holder is inserted between the holding arms parallel or at 90 degrees to the edge of the corrugated bottom or the sterilization tray.

When the webs of the corrugated bottom are set at 45 degrees to the edge of the corrugated bottom, the two crosspieces can immerse particularly deep in the two recesses or notches near the edge and the main section is weakened as little as possible if the two recesses or notches near the edge are mirror-symmetrical to the central axis and each have three edges that are set approximately at right angles to each other. Then two of the four webs of the relevant crosspiece can be arranged in the two corners of the respective recess or notch near the edge. The two recesses or notches can also serve as a positioning aid.

In a basically similar manner the larger version allows for a particularly deep immersion of the central crosspiece in the further recess formed as a through recess, and/or for the lowest possible weakening of the main section, if the through recess is rectangular and if the four webs of the crosspiece in question are arranged in the four corners of the through recess. In this configuration, too, the through recess can serve as a positioning aid.

The silicone bar of the instrument holder is preferably held under the holding sections formed on the free end sections of the four holding arms and possibly also of the two intermediate arms.

As an alternative to the favorable immersion of the main section from below into the corrugated bottom, it is also possible to mount the at least one fixing clip on the corrugated bottom from below. In this case, crosspieces of a lower height are respectively received between the holding arms of the two rows of arms. This lower mounting position, too, is defined mechanically and provides a secure hold for the fixing clip on the corrugated bottom. Even in the lower mounting position the main section of the fixing clip is flat. However, it protrudes downwards from the corrugated bottom and serves as a foot, so to speak.

DETAILED DESCRIPTION

Three embodiments of the present disclosure are described below based on the associated figures.

Figure 1:
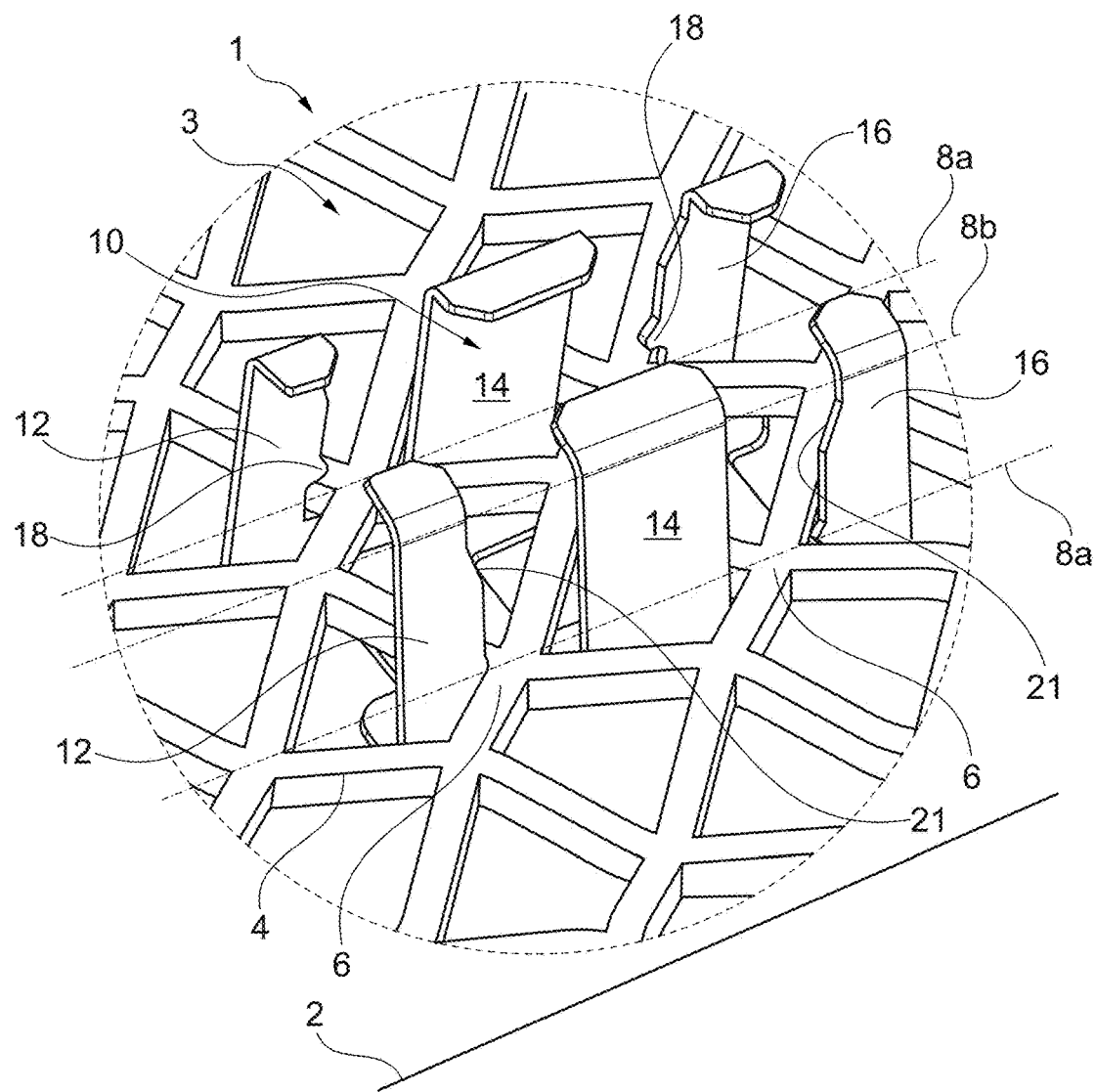
FIG. 1 is a perspective view from above illustrating an arrangement according to a first embodiment of the present disclosure.

FIG. 1 shows an arrangement according to a first embodiment of the present disclosure. It has a sterilization tray 1, of which only one of its edges 2 and a section of its corrugated bottom 3 are shown. The corrugated bottom 3 has a perforated grid formed from webs 4 arranged at right angles to one another (in a top view). The webs 4 are preferably set at 45° to the edge 2. Four webs 4 each form a crosspiece 6.

Parallel to the edge 2 of sterilization tray 1, rows of crosspieces 8a, 8b extend at two different heights, with a lower row of crosspieces 8a and an upper row of crosspieces 8b always being provided alternately. Consequently, it is of course possible to deviate from the indicated angle, both upwards and downwards, as long as a corresponding waveform results.

As shown in FIG. 1, a larger version of the fixing clip 10 as disclosed is inserted through the perforated grid openings at right angles (when seen in a top view) and clipped. More specifically, a first row of arms and a second row of arms extend in parallel to the rows of crosspieces 8a, 8b and to the edge 2, each row of arms having a first holding arm 12, an intermediate arm 14 formed as a lug, and a second holding arm 16. The two intermediate arms 14 are designed to be so narrow that they extend through a respective opening in the perforated grid without direct contact with the webs 4 or the crosspieces 6. The four holding arms 12, 16 each have a snap-in nose 18, which rests against the upper side of a crosspiece 6. Thus, the fixing clip 10 is clipped to the corrugated bottom 3 of the sterilization tray 1.

On the four holding arms 12, 16, respective lead-in chamfers 21 are formed above the respective snap-in nose 18. This forms an insertion aid for each of the four crosspieces 6 concerned.

Figure 2:
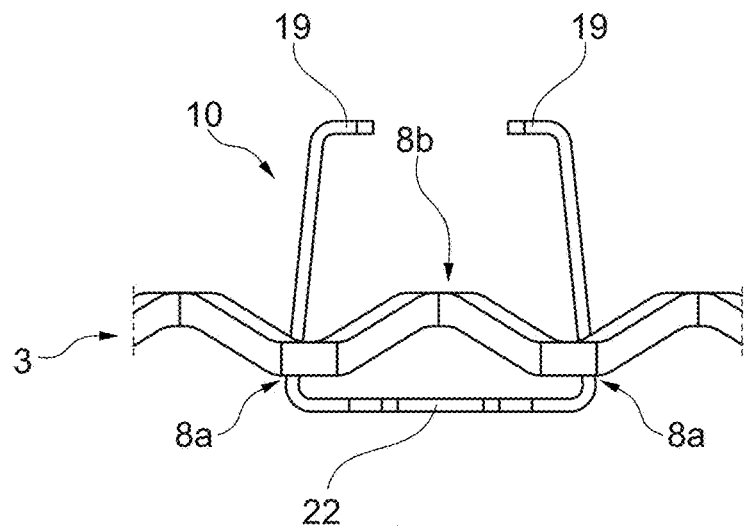
FIG. 2 is a further illustration of the first embodiment of the arrangement from FIG. 1.

FIG. 2 is a further representation of the first embodiment of the arrangement from FIG. 1, viewed along the rows of crosspieces 8a, 8b. Holding sections 19 are formed on the upper end sections of holding arms 12, 16 and of intermediate arms 14, which embrace a silicone bar of the instrument holder (not shown), which is thus also arranged in parallel to the rows of crosspieces 8a, 8b.

According to FIG. 2, the fixing clip 10 is clipped onto two lower rows of crosspieces 8a, so that a flat main section 22 of the fixing clip 10 is arranged under the corrugated bottom 3. This so-called lower mounting position of the fixing clip 10 is also possible.

Figure 4:
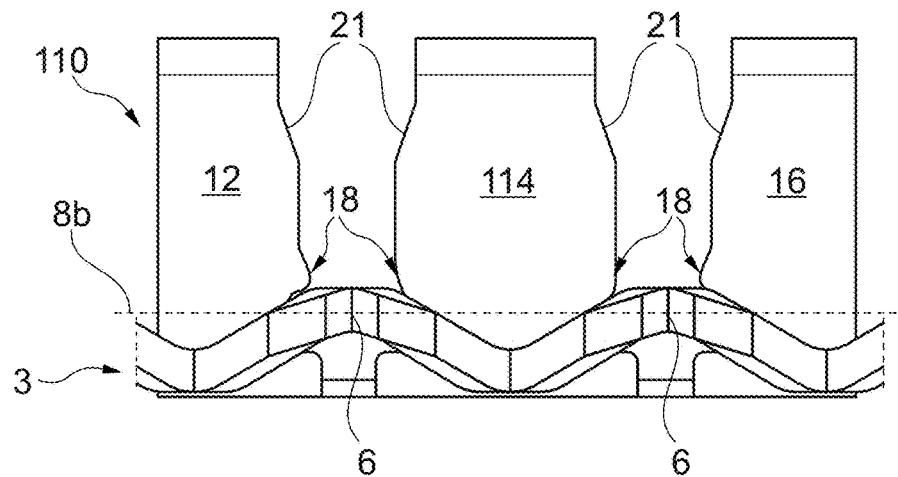
FIG. 4 is a side view of an arrangement of the second embodiment of the fixing clip from FIG. 3.
Figure 7:
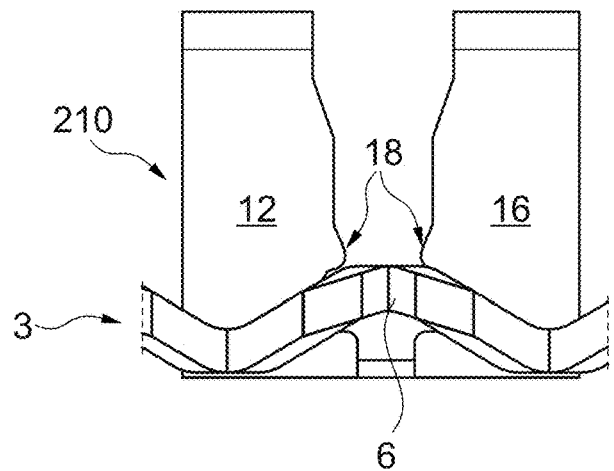
FIG. 7 is a side view of an arrangement of the third embodiment of the fixing clip from FIG. 6.

If, on the other hand, an upper mounting position is selected it is possible that the main section 22 is arranged above the lower row of crosspieces 8a and thus completely immerses in the corrugated bottom 3. FIGS. 4 and 7 respectively show fixing clips 110, 210 in the upper mounting position.

Figure 3:
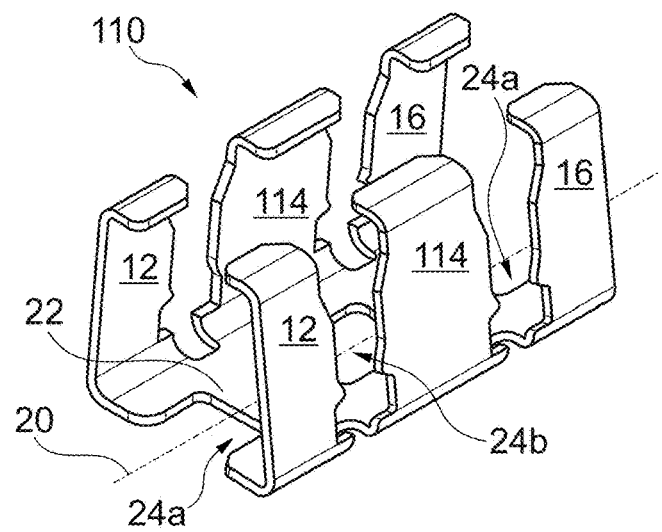
FIG. 3 is a view of a fixing clip according to a second embodiment of the present disclosure.

FIG. 3 is a representation of a fixing clip 110 according to a second embodiment of the present disclosure.

First, the features corresponding to the fixing clip 10 of FIG. 1 are explained: The fixing clip 10, 110 is a bent sheet metal part. Two rows of arms, each with a first holding arm 12, an intermediate arm 14, 114 and a second holding arm 16, extend along a center axis 20, which is an axis of symmetry. The main section 22 is located between the two rows of arms. Three recesses 24a, 24b are provided in the main section 22, into each of which a crosspiece 6 of a lower row of crosspieces 8a can immerse from above. More specifically, two outer recesses 24a and a further recess 24b formed as a central through recess are provided. The two outer recesses 24a are U-shaped and arranged at the edge of the main section 22.

Figure 5:
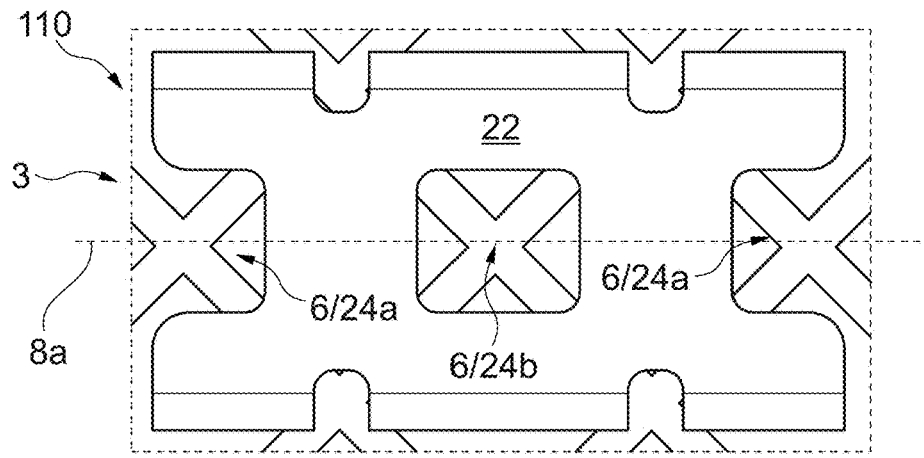
FIG. 5 is a further illustration of the second embodiment of the arrangement from FIG. 4 from below.

In contrast to the first embodiment of fixing clip 10 from FIG. 1, the second fixing clip 110 according to FIGS. 3 to 5 not only has snap-in noses 18 on the holding arms 12, 16, but also has a further snap-in nose 18 on each intermediate arm 114 on both sides. Each snap-in nose 18 of the intermediate arm 114 extends against a snap-in nose 18 of a holding arm 12, 16.

FIG. 4 is a side view of an arrangement with the corrugated bottom 3 from FIG. 1 and with the second embodiment of fixing clip 110 from FIG. 3, in which the four snap-in noses 18 of a row of arms are clearly shown. Thus, each row of arms can come into contact with two crosspieces 6 and hold the crosspiece 6 on both sides.

On the four holding arms 12, 16 and on the two intermediate arms 114, respective lead-in chamfers 21 are formed above the snap-in noses 18. This creates a v-shaped insertion funnel for each of the four crosspieces 6 concerned.

FIG. 5 is a further representation of the second embodiment of the arrangement from FIG. 4 from below. Here the main section 22 is shown in full, with a crosspiece 6 of the lower row of crosspieces 8a being received in each of the three recesses 24a, 24b. Thus, the upper mounting position is obtained, in which the main section 22 does not affect the storage position of the sterilization tray 1, even if it has no feet.

Figure 6:
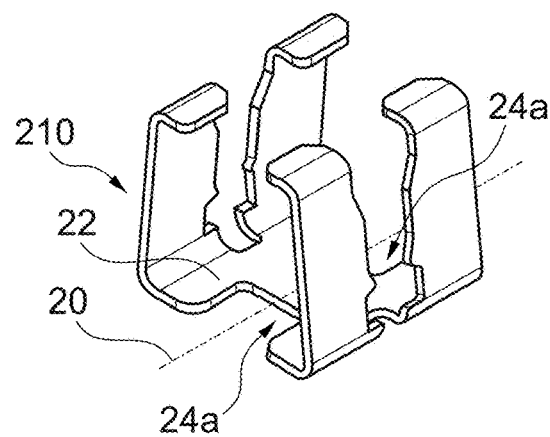
FIG. 6 is a view of a fixing clip according to a third embodiment of the present disclosure.

FIG. 6 is a representation of a fixing clip 210 according to a third embodiment of the present disclosure. It is the so-called smaller version, which is shorter along the central axis 20 than the two larger versions shown in FIGS. 1 to 5. In the third embodiment, the two intermediate arms 14 have been omitted.

FIG. 7 is a side view of an arrangement with the third embodiment of the fixing clip 210 from FIG. 6. It is to be recognized that the two holding arms 12, 16 of each row of arms directly receive only one crosspiece 6 between them.

Figure 8:
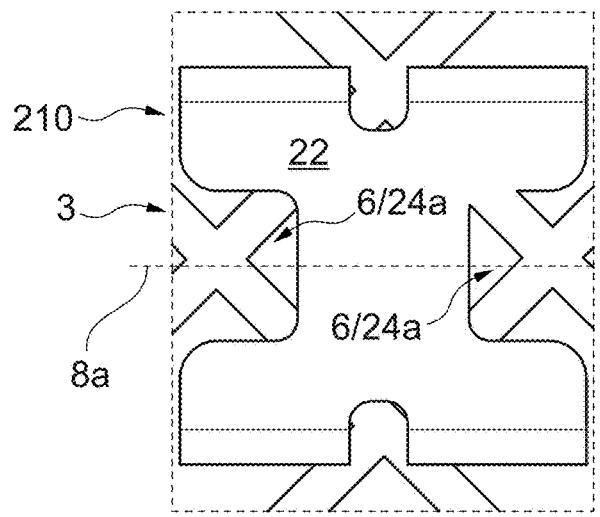
FIG. 8 is a further representation of the third embodiment of the arrangement from FIG. 7 from below.

FIG. 8 is a further representation of the third embodiment of the arrangement from FIG. 7 from below. In the third embodiment, the further recess 24b on the main section 22 is omitted, since only two crosspieces 6 of the lower row of crosspieces 8a have to immerse in a respective recess 24a.

FIGS. 4, 5, 7 and 8 show the fixing clips 110; 210 in the preferred higher mounting position on the corrugated bottom 3 of the sterilization tray 1, in which the two rows of arms each are operatively connected to an upper row of crosspieces 8b, while the recesses 24a, 24b receive crosspieces 6 of a lower row of crosspieces 8a.

In summary, the above embodiments hence show a fixing clip that is laid out for tool-free mounting on the perforated or grid-like corrugated bottom 3 of a sterilization tray. For this purpose, the fixing clip has at least the following features:

A preferably plate-shaped or tongue-shaped main section or base plate 22, on which two rows of arms are arranged or formed opposite each other with respect to a center or longitudinal axis 20 of the tongue-shaped (in top view essentially rectangular) main section. That is to say, a plurality of preferably plate-shaped arms are formed or arranged on each longitudinal side of the tongue-shaped main section which each are spaced apart from one another in the longitudinal direction of the main section.

Each row of arms has at least a first holding arm 12 and a second holding arm 16, which extend essentially perpendicularly or at an angle of about 90° to the plate-/tongue-shaped main section 22.

A snap-in nose 18 or snap-in projection is formed on the side edges facing each other of at least two of the arms of each longitudinal side/row of arms, which lie opposite each other and point towards each other.

A first edge extends along the main section 22 between the first two holding arms 12 and a second edge extends between the second two holding arms 16, with a recess 24a or notch being formed on each of the two edges. In other words, preferably rectangular recesses 24a or notches are formed on the longitudinally spaced end edges of the (plate-/tongue-shaped) main section 22, which extend in the longitudinal direction. The corners of the preferably rectangular recesses 24a are preferably rounded.

This means that the fixing clip has at least four clip arms 12, 16 with snap-in noses 18 opposite each other, which are formed or arranged on the common base plate (main section) 22 and extend away at an angle of about 90° (plus/minus 20°), with at least two clip arms always being arranged, longitudinally spaced apart from one another, on two opposite longitudinal sides of the base plate 22. At least one, preferably rectangular, recess 24a, 24b is formed in the base plate 22. This can be formed as a hole-like recess 24b, closed all around, in a central area of the base plate 22 and/or as a partially open notch-like recess 24a on at least one end edge (transverse side) connecting the two longitudinal sides or on both end edges (transverse sides) of the base plate 22.

LIST OF REFERENCE SIGNS

1 Sterilization tray
2 Edge of sterilization tray
3 Corrugated bottom
4 Web
6 Crosspiece
8a Lower row of crosspieces
8b Upper row of crosspieces
10 Larger version of fixing clip (first variant)
12 First holding arm
14 Intermediate arm
16 Second holding arm
18 Snap-in nose
19 Holding section
20 Center axis
21 Lead-in chamfer
22 Main section
24a Recess
24b Further recess
110 Larger version of the fixing clip (second variant)
114 Intermediate arm
210 Smaller version of the fixing clip

The invention claimed is:

1. A fastening clamp that is adapted and configured for attachment without tools to a perforated undulating base of a sterilization sieve basket, wherein the fastening clamp has a main portion on which two rows of arms are arranged opposite each other with respect to a central axis, wherein each row of arms has a first retaining arm and a second retaining arm, on each of which a respective latching nose is formed, wherein the latching noses of the two retaining arms of each row of arms face toward each other, and wherein a first edge extends on the main portion between the two first retaining arms and a second edge extends between the two second retaining arms, characterized in that a cutout or recess is formed on each of the two edges.

2. The fastening clamp according to claim 1, wherein the two cutouts or recesses extend transversely to the central axis over at least one third of a respective width of the main portion or of a respective distance of the opposite retaining arms.

3. The fastening clamp according to claim 1, wherein the two cutouts or recesses along the central axis each extend over at least one-eighth of a length of the main portion.

4. The fastening clamp according to claim 1, wherein a respective intermediate arm is provided between the two retaining arms of a row of arms, and wherein a further recess is provided approximately in the center of the main portion, which is configured as a passage recess.

5. The fastening clamp according to claim 4, wherein holding portions, preferably at least three holding portions, are formed on free end portions of the intermediate arms and/or on first retaining arms and/or on second retaining arms.

6. The fastening clamp according to claim 5, wherein the holding portions are provided opposite each other in pairs, preferably facing each other in pairs.

7. The fastening clamp according to claim 4, wherein a further latching nose is provided on each of the two intermediate arms, which extends counter to the latching nose of the first retaining arm.

8. The fastening clamp according to claim 4, wherein the intermediate arm is a tab on which a respective straight edge portion is formed opposite the latching noses of the two adjacent retaining arms.

9. The fastening clamp according to claim 4, wherein the passage recess is substantially rectangular.

10. The fastening clamp according to claim 1, wherein insertion chamfers are formed above the latching noses.

* * * * *